US009837067B2

(12) United States Patent
Kleiss et al.

(10) Patent No.: US 9,837,067 B2
(45) Date of Patent: Dec. 5, 2017

(54) METHODS AND SYSTEMS FOR PROVIDING AUDITORY MESSAGES FOR MEDICAL DEVICES

(75) Inventors: James Alan Kleiss, Oconomowoc, WI (US); Emil Markov Georgiev, Hartland, WI (US); Scott William Robinson, Bayside, WI (US)

(73) Assignee: General Electric Company, Schenectady, NY (US)

(*) Notice: Subject to any disclaimer, the term of this patent is extended or adjusted under 35 U.S.C. 154(b) by 867 days.

(21) Appl. No.: 13/416,924

(22) Filed: Mar. 9, 2012

(65) Prior Publication Data

US 2013/0238314 A1 Sep. 12, 2013

Related U.S. Application Data

(60) Provisional application No. 61/505,395, filed on Jul. 7, 2011.

(51) Int. Cl.

| | |
|---|---|
| ***G06F 17/27*** | (2006.01) |
| ***A61B 5/04*** | (2006.01) |
| ***A61B 5/00*** | (2006.01) |
| ***G10L 13/033*** | (2013.01) |
| ***G10L 21/003*** | (2013.01) |

(52) U.S. Cl.
CPC .......... *G10L 13/033* (2013.01); *G10L 21/003* (2013.01)

(58) Field of Classification Search
CPC .................................................. G06F 17/2785
USPC ..................................................... 704/9, 274
See application file for complete search history.

(56) References Cited

U.S. PATENT DOCUMENTS 5,438,607 A 8/1995 Przygoda, Jr. et al.
5,441,047 A * 8/1995 David .................. A61B 5/6887 128/904
5,785,650 A * 7/1998 Akasaka ............ A61N 1/37282 128/904
6,450,172 B1 * 9/2002 Hartlaub ............ A61N 1/37217 128/899
6,727,814 B2 4/2004 Saltzstein et al.
7,138,575 B2 * 11/2006 Childs, Jr. .............. G06Q 40/00 700/94
7,508,307 B2 3/2009 Albert
7,742,807 B1 * 6/2010 Walls ................... A61B 5/0402 600/509
8,775,196 B2 * 7/2014 Simpson ............. G06F 19/3418 705/2
2004/0121767 A1 6/2004 Simpson et al.
2004/0172222 A1 9/2004 Simpson et al.
2005/0055242 A1 * 3/2005 Bello .................. G06F 19/3468 705/2

(Continued)

*Primary Examiner* — David Hudspeth
*Assistant Examiner* — Timothy Nguyen
(74) *Attorney, Agent, or Firm* — Dean D. Small; The Small Patent Law Group, LLC

(57) ABSTRACT

Methods and systems for providing auditory messages for medical devices are provided. One method includes receiving semantic rating scale data corresponding to a plurality of sounds and medical message descriptions and performing semantic mapping using the received semantic rating scale data. The method also includes determining profiles for audible medical messages based on the semantic mapping and generating audible medical messages based on the determined profiles.

19 Claims, 9 Drawing Sheets

(56) References Cited

U.S. PATENT DOCUMENTS

| | | | | | |
|---|---|---|---|---|---|
| 2005/0065817 | A1* | 3/2005 | Mihai | A61B 5/0002 | 705/2 |
| 2005/0151640 | A1* | 7/2005 | Hastings | A61B 5/411 | 340/539.11 |
| 2005/0188853 | A1 | 9/2005 | Scannell, Jr. | | |
| 2005/0288563 | A1 | 12/2005 | Feliss et al. | | |
| 2005/0289092 | A1* | 12/2005 | Sumner, II | G06F 19/3437 | 706/46 |
| 2006/0103541 | A1* | 5/2006 | Esson | G08B 3/10 | 340/686.6 |
| 2007/0073745 | A1* | 3/2007 | Scott | G06F 17/30737 | |
| 2007/0106126 | A1* | 5/2007 | Mannheimer | A61B 5/14551 | 600/300 |
| 2008/0001735 | A1* | 1/2008 | Tran | G06F 19/3418 | 340/539.22 |
| 2008/0198023 | A1* | 8/2008 | Hansen | A61B 5/0002 | 340/573.1 |
| 2010/0022902 | A1* | 1/2010 | Lee | A61B 5/0006 | 600/509 |
| 2010/0030576 | A1* | 2/2010 | Gregory | G06F 19/345 | 705/3 |
| 2010/0234718 | A1* | 9/2010 | Sampath | A61B 5/411 | 600/407 |
| 2010/0286490 | A1* | 11/2010 | Koverzin | G06F 19/3418 | 600/301 |
| 2010/0312095 | A1 | 12/2010 | Jenkins et al. | | |
| 2011/0015493 | A1* | 1/2011 | Koschek | A61B 5/0002 | 600/300 |
| 2011/0172740 | A1* | 7/2011 | Matos | A61N 1/37264 | 607/60 |
| 2011/0201951 | A1* | 8/2011 | Zhang | A61B 5/0456 | 600/509 |
| 2011/0304460 | A1* | 12/2011 | Keecheril | G06Q 10/087 | 340/572.1 |
| 2012/0123241 | A1 | 5/2012 | Stilley et al. | | |
| 2012/0123242 | A1 | 5/2012 | Stilley et al. | | |
| 2012/0271372 | A1* | 10/2012 | Osorio | A61B 5/7275 | 607/17 |
| 2012/0330557 | A1* | 12/2012 | Zhang | A61B 6/503 | 702/19 |

* cited by examiner

140

142 144 146 148 150

| | F1 | F2 | F3 | F4 |
|---|---|---|---|---|
| Reassuring/Disturbing | 0.74 | 0.16 | -0.35 | 0.03 |
| Relaxed/Tense | 0.69 | 0.08 | -0.33 | -0.37 |
| Healthy/Sick | 0.67 | 0.17 | -0.21 | 0.03 |
| Submissive/Assertive | 0.59 | -0.03 | -0.05 | -0.53 |
| Typical/Unusual | 0.08 | 0.88 | -0.08 | 0.16 |
| Frequent/Rare | 0.09 | 0.84 | -0.01 | 0.17 |
| Common/Unexpected | 0.07 | 0.83 | 0.24 | 0.01 |
| Ordinary/Imaginative | 0.22 | 0.67 | 0.04 | 0.02 |
| Unpolished/Elegant | -0.16 | -0.01 | 0.76 | -0.10 |
| Dissatisfying/Satisfying | -0.24 | -0.14 | 0.74 | -0.11 |
| Discordant/Harmonious | -0.24 | -0.24 | 0.73 | 0.11 |
| Agitated/Calm | -0.51 | -0.05 | 0.59 | 0.31 |
| Vague/Precise | -0.08 | 0.21 | -0.08 | 0.79 |
| Unreliable/Trustworthy | 0.04 | 0.25 | -0.11 | 0.78 |
| Unimportant/Urgent | -0.38 | 0.09 | 0.17 | 0.69 |
| Yielding/Firm | 0.03 | -0.10 | 0.40 | 0.67 |
| Indistinct/Distinct | -0.39 | 0.04 | -0.32 | 0.60 |
| Delicate/Strong | -0.46 | 0.09 | 0.08 | 0.53 |

FIG. 8

168

| Medical Message\Quality Attribute (169) | Disturbing (171) | Unusual (173) | Elegant (175) | Precise (177) |
|---|---|---|---|---|
| Non-Critical Device (Message: No Sound) | Low | Low | Medium | Medium |
| Extreme High Urgency Condition (No Sound) | High | Medium | Low | High |
| High Urgency Alarm (Turned Off) | High | High | Low | High |
| IEC High Urgency Alarm | High | Medium | Medium | High |
| Device Info / Feedback | Medium | Medium | Medium | Medium |
| Device Process Begun | Low | Medium | Medium | Medium |
| IEC Low Urgency Alarm | Medium | Low | Low | Medium |
| Unassigned | Low | High | High | Low |
| Unassigned | Low | Medium | High | Low |
| Unassigned | Medium | High | Medium | Low |

FIG. 10

METHODS AND SYSTEMS FOR PROVIDING AUDITORY MESSAGES FOR MEDICAL DEVICES

CROSS REFERENCE TO RELATED APPLICATIONS

This application claims priority to and the benefit of the filing date of U.S. Provisional Application No. 61/505,395, filed Jul. 7, 2011, the subject matter of which is hereby incorporated by reference in its entirety.

BACKGROUND OF THE INVENTION

The subject matter disclosed herein relates generally to audible messages, and more particularly to a methods and systems for providing audible notifications for medical devices.

In medical environments, especially complex medical environments where multiple patients may be monitored for multiple medical conditions, standardization of alarms and/or warnings creates significant potential for confusion and inefficiency on the part of users (e.g., clinicians or patients) in responding to specific messages. For example, it is sometimes difficult for clinicians and/or users of medical devices to distinguish or quickly identify the source and condition of a particular audible alarm or warning. Accordingly, the effectiveness and efficiency with which users respond to medical messaging can be adversely affected, which can lead to delays to responding to medical or system conditions associated with these audible alarms or warnings.

In particular, medical facilities typically include rooms to enable surgery to be performed on a patient, to enable a patient's medical condition to be monitored, and/or to enable a patient to be diagnosed. At least some of these rooms include multiple medical devices that enable the clinician to perform the operation, monitoring, and/or diagnosis. During operation of these medical devices, at least some of the devices are configured to emit audible indications, such as audible alarms and/or warnings that are utilized to inform the clinician of a medical condition being monitored. For example, a heart monitor and a ventilator may be attached to a patient. When a medical condition arises, such as low heart rate or low respiration rate, the heart monitor or ventilator emits an audible indication that alerts and prompts the clinician to perform some action.

Under certain conditions or in certain medical environments, multiple medical devices may concurrently generate audible indications. In some instances, two different medical devices may generate the same audible indication or an indistinguishably similar audible indication. For example, the heart monitor and the ventilator may both generate a similar high-frequency sound when an urgent condition is detected with the patient, which is output as the audible indication. Therefore, under certain conditions, the clinician may not be able to distinguish whether the alarm condition is being generated by the heart monitor or the ventilator. In this case, the clinician visually observes each medical device to determine which medical device is generating the audible indication. Moreover, when three, four, or more medical devices are being utilized, it is often difficult for the clinician to easily determine which medical device is currently generating the audible indication. Thus, delay in taking action may result from the inability to distinguish the audible indications from the different devices. Additionally, in some instances the clinician is not able to associate the audible indication with a specific condition and accordingly must visually view the medical device to assess a course of action.

Moreover, in some instances, no alarms and/or warnings exist for certain conditions, which can result in adverse results, such as injury to patients. For example, movement of major parts of medical equipment (e.g., CT/MR table and cradle, interventional system table/C-arm, etc.) is known for creating a potential for pinch points and collisions. In the majority of these cases, the only indication for these movements, especially for users not controlling the movements and for the patients is direct visual contact, which is not always possible.

SUMMARY OF THE INVENTION

In one embodiment, a method for generating an audible medical message is provided. The method includes receiving semantic rating scale data corresponding to a plurality of sounds and medical message descriptions and performing semantic mapping using the received semantic rating scale data. The method also includes determining profiles for audible medical messages based on the semantic mapping and generating audible medical messages based on the determined profiles.

In another embodiment, a method for generating an audible medical message is provided. The method includes defining an audible signal to include an acoustical property based on a semantic sound profile that corresponds to a medical message for a medical device. The method also includes broadcasting the audible signal using the medical device.

In yet another embodiment, a medical arrangement is provided that includes a plurality of medical devices capable of generating different medical messages. The medical arrangement also includes a processor in each of the medical devices configured to generate an audible signal that includes an acoustical property based on a semantic sound profile that corresponds to one of the medical messages.

BRIEF DESCRIPTION OF THE DRAWINGS

FIG. 8 is a table illustrating bipolar attribute pairs sorted by factor loadings in accordance with various embodiments.

FIG. 10 is a table illustrating an approximation of the graph of FIG. 9.

DETAILED DESCRIPTION OF THE INVENTION

Figure 1:
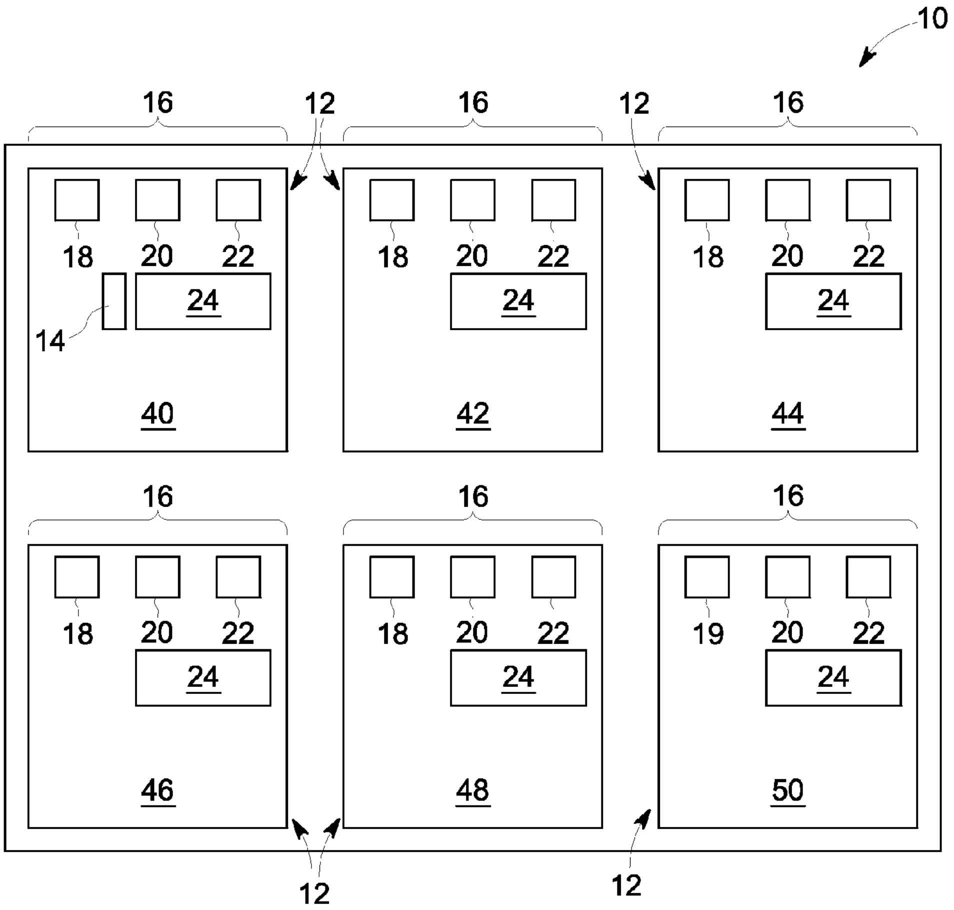
FIG. 1 is block diagram of an exemplary medical facility in accordance with various embodiments.

The following detailed description of certain embodiments will be better understood when read in conjunction with the appended drawings. The figures illustrate diagrams of the functional blocks of various embodiments. The functional blocks are not necessarily indicative of the division between hardware circuitry. Thus, for example, one or more of the functional blocks (e.g., processors or memories) may be implemented in a single piece of hardware (e.g., a general purpose signal processor or a block or random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings.

Various embodiments provide methods and systems for providing audible indications or messages, particularly audible alarms and warnings for devices, especially medical devices. For example, a classification system may be provided, as well as a semantic mapping for these audible indications or messages.

As described in more detail herein, the various embodiments provide for the differentiation of audible notifications or messages, such as alarms or warnings based on acoustical and/or musical properties that convey specific semantic character(s). Additionally, these audible notifications or messages also may be used to provide an auditory means to indicate device movements, such as movement of major equipment pieces. It should be noted that although the various embodiments are described in connection with medical systems having particular medical devices, the various embodiments may be implemented in connection with medical systems having different devices or non-medical systems. The various embodiments may be implemented generally in any environment or in any application to distinguish between different audible indications or messages associated or corresponding to a particular event or condition for a device or process.

Moreover, as used herein, an audible indication or message refers to any sound that may be generated and emitted by a machine or device. For example, audible indications or alarms may include auditory alarms or warnings that are specified in terms of frequency, duration and/or volume of sound.

FIG. 1 is block diagram of an exemplary healthcare facility 10 in which various embodiments may be implemented. The healthcare facility 10 may be a hospital, a clinic, an intensive care unit, an operating room, or any other type of facility for healthcare related applications, such as for example, a facility that is used to diagnose, monitor or treat a patient. Accordingly, the healthcare facility 10 may also be a doctor's office or a patient's home.

In the exemplary embodiment, the facility 10 includes at least one room 12, which are illustrated as a plurality of rooms 40, 42, 44, 46, 48, and 50. At least one of the rooms 12 may include different medical systems or devices, such as a medical imaging system 14 or one or more medical devices 16 (e.g., a life support system). The medical systems or devices may be, for example, any type of monitoring device, treatment delivery device or medical imaging device, among other devices. For example, different types of medical imaging devices or medical monitors include a Computed Tomography (CT) imaging system, an ultrasound imaging system, a Magnetic Resonance Imaging (MRI) system, a Single-Photon Emission Computed Tomography (SPECT) system, a Positron Emission Tomography (PET) system, an Electro-Cardiograph (ECG) system, an Electroencephalography (EEG) system, etc. It should be realized that the systems are not limited to the imaging and/or monitoring systems described above, but may be utilized with any medical device configured to emit a sound as an indication to an operator.

Thus, at least one of the rooms 12 may include a medical imaging device 14 and a plurality of medical devices 16. The medical devices 16 may include, for example, a heart monitor 18, a ventilator 20, anesthesia equipment 22, and/or a medical imaging table 24. It should be realized that the medical devices 16 described herein are exemplary only, and that the various embodiments described herein are not limited to the medical devices shown in FIG. 1, but may also include a variety of medical devices utilized in healthcare applications.

Figure 2:
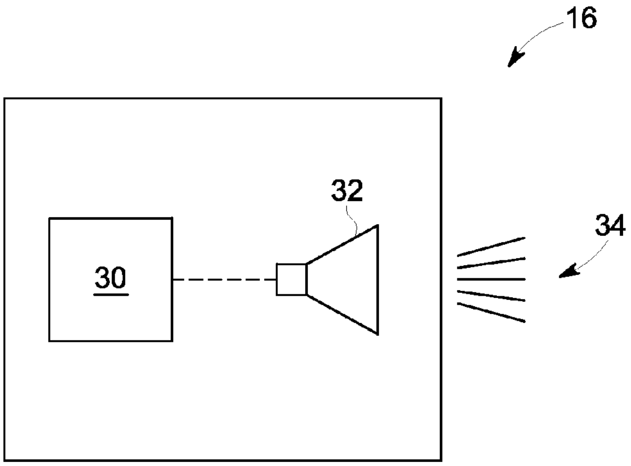
FIG. 2 is a block diagram of an exemplary medical device in accordance with various embodiments.

FIG. 2 is a simplified block diagram of the medical device 16 shown in FIG. 1. In the exemplary embodiment, the medical device 16 includes a processor 30 and a speaker 32. In operation, the processor 30 is configured to operate the speaker 32 to enable the speaker 32 to output an audible indication 34, which may be referred to as an audible message, such as an audible medical message, for example, an auditory alarm or warning. It should be noted that the processor 30 may be implemented in hardware, software, or a combination thereof. For example, the processor 30 may be implemented as, or performed, using tangible non-transitory computer readable medium. It should be noted that the medical imaging systems 14 may include similar components.

In operation, the audible indications/messages generated by the medical imaging systems 14 and/or each medical device 16 creates an audible landscape that enables a clinician to audibly identify which medical device 16 is generating the audible indication and/or message and/or the type of message (e.g., the severity of the message) without viewing the particular medical device 16. The clinician may then directly respond to the audible indication and/or message by visually observing the medical imaging system 14 or device 16 that is generating the audible indication without the need to observe, for example, several of the medical devices 16, if not desired.

In various embodiments, the audible indication 34, which may be a complex auditory indication, is semantically related to a particular medical message, such as corresponding to a specific medical alarm or warning, or to indicate movement of a piece of equipment, such as a scanning portion of the medical imaging system 14. The audible indication 34 in various embodiments enables two or more medical systems or devices, such as the heart monitor 18 and the ventilator 20 to be concurrently monitored audibly by the operator, such that different alarms and/or warning sounds may be differentiated on the basis of acoustical and/or musical properties that convey a specific semantic character. Thus, the various audible indications 34 generated by the medical imaging system 14 and/or the various medical devices 16 provides a set of indications and/or messages that operate with each other to provide a soundscape for this particular environment. The set of sounds, which may include multiple audible indications 34, may be customized for a particular environment. For example, the audible indications 34 that produce the set of sounds for an operating room may be different than the audible indications 34 that produce the set of sounds for a monitoring room.

Additionally, the audible indications 34 may be utilized to inform a clinician that a medical device is being repositioned. For example, an audible indication 34 may indicate that the table of a medical imaging device is being repositioned. The audible indication 34 may indicate that a portable respiratory monitor is being repositioned, etc. In each case, the audible indication 34 generated for each piece of equipment may be differentiated to enable the clinician to audibly determine that either the table or the respiratory monitor, or some other medical device is being repositioned. Other medical devices that may generate a distinct audible indication 34 include, for example, a radiation detector, an x-ray tube, etc. Thus, each medical device 16 may be programmed to emit an audible indication/message based on an alarm condition, a warning condition, a status condition, or a movement of the medical device 16 or medical imaging system 14.

In various embodiments, the audible indication 34 is designed and/or generated based on different criteria, such as different acoustical and/or musical properties that convey a specific semantic character. In general, a set of medical messages or audible indications 34 that are desired to be broadcast to a clinician may be determined, for example, initially selected. In one embodiment, the audible indications 34 may be used to inform listeners that a particular medical condition exists and/or to inform the clinician that some action potentially needs to be performed. Thus, each audible indication 34 may include different elements or acoustical properties. For example, one of the acoustical properties enables the clinician to audibly identify the medical device generating the audible message and a different second acoustical property enables the clinician to identify the type of the audible alarm/warning, movement, or when any operator interaction is required. Moreover, other acoustical properties may communicate the medical condition (or patient status) to the clinician. For example, how the audible indication/message is broadcast, and the tone, frequency, and/or timbre of the audible indication may provide information regarding the severity of the alarm or warning, such as that a patient's heart is stopped, breathing has ceased, the imaging table is moving, etc.

Figure 3:
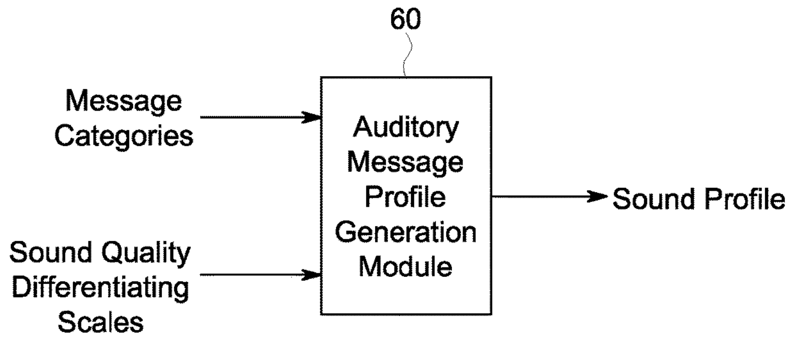
FIG. 3 is a diagram illustrating an auditory message profile generation module formed in accordance with various embodiments.

In particular, various embodiments provide a conceptual framework and a perceptual framework for defining audible indications or messages. In some embodiments, sound profiles for medical images are defined that are used to generate the audible indications 34. The sound profiles map different audible messages to sounds corresponding to the audible indications 34, such as to indicate a particular condition or operation. For example, as shown in FIG. 3, an auditory message profile generation module 60 may be provided to generate or identify different sounds profiles. The auditory message profile generation module 60 may be implemented in hardware, software or a combination thereof, such as part of or in combination with the processor 30. However, in other embodiments, the auditory message profile generation module 60 may be a separate processing machine wherein all of some of the methods of the various embodiments are performed entirely with one processor or different processors in different devices.

The auditory message profile generation module 60 receives as an input defined message categories, which may correspond, for example, to medical alarms or indications. The auditory message profile generation module 60 also receives as an input a plurality of defined quality differentiating scales. The inputs are based on a semantic rating scale as described in more detail herein and are processed or analyzed to define or generate a plurality of sound profiles that may be used to generate, for example, audible alarms or warnings. In various embodiments, the auditory message profile generation module 60 uses at least one of a hierarchical cluster analysis or a principal components factor analysis to define or generate the plurality of sound profiles.

For example, various embodiments classify medical auditory messages into a plurality of categories, which may correspond to the conceptual model of clinicians working in ICU environments. In one embodiment, the medical auditory messages are classified into seven categories, which include the following auditory message types:

1. Non-critical Device message;
2. Extreme high urgency condition;
3. Extreme high urgency message;
4. International Electrotechnical Commission (IEC) high urgency alarm;
5. Device info./feedback;
6. Device process began; and
7. IEC low urgency alarm It should be noted that the conceptual model may result in categories not related to medical messages and that may be utilized for additional purposes in clinical environments.

In various embodiments, a set of sound quality differentiating scales that describe the medical auditory design space are also defined. For example, in one embodiment, a set of four sound quality differentiating scales may define sound quality axes as follows:

1. Discordance . . . Concordance;
2. Resolved . . . Unresolved;
3. Hard attack . . . Soft attack; and
4. Novelty . . . Familiarity.

Figure 4:
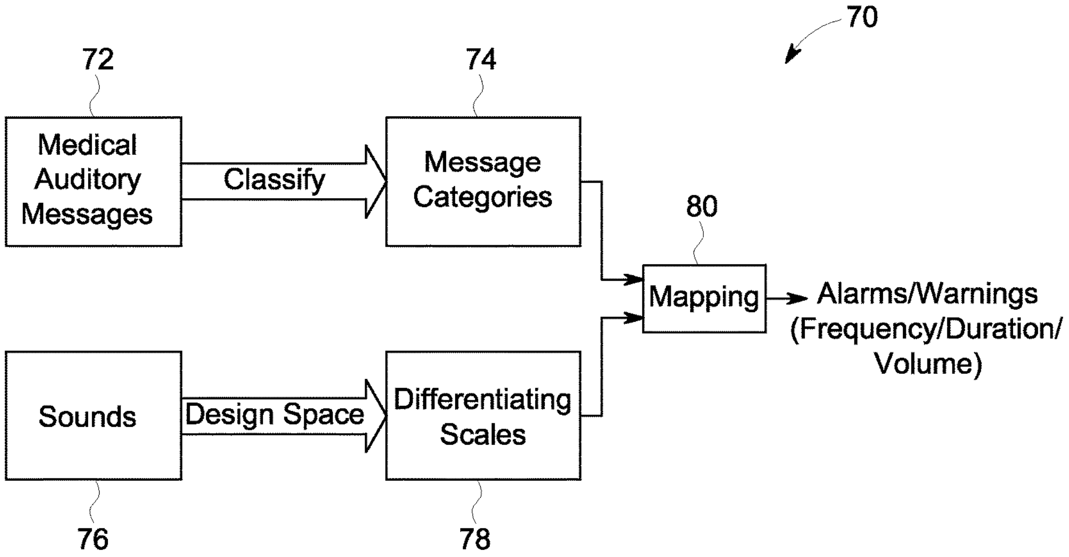
FIG. 4 is a diagram illustrating a mapping process flow in accordance with various embodiments.

Thus, in this embodiment, the seven different categories of medical auditory messages may be mapped to the four sound qualities differentiating scales to generate the plurality of sound profiles. For example, as shown in FIG. 4, illustrating a mapping process flow 70 in accordance with various embodiments, a plurality of medical messages 72 are classified into message categories 74. Additionally, a plurality of sounds 76 defines a design space that includes sound quality differentiating scales 78. It should be noted that the medical auditory messages 72 and the sounds 76 may be identified or determined using different suitable methods and as described in more detail herein. For example, in some embodiments, the auditory messages 72 may correspond to defined or predetermined medical alarms or warnings and the sounds 76 may correspond to defined or predetermined sounds used in different medical devices or combination thereof. However, in some embodiments, the auditory messages 72 and/or sounds 76 may be non-defined in particular applications, for example, in a medical environment.

As shown in FIG. 4, a mapping 80 is determined for the message categories 74 and the differentiating scales 78, which is then used to generate audible alarms and/or warnings. For example, the mapping may define sound profiles that may generate sounds for the audible alarms and/or warnings that have a particular frequency, duration and/or volume.

Figure 5:
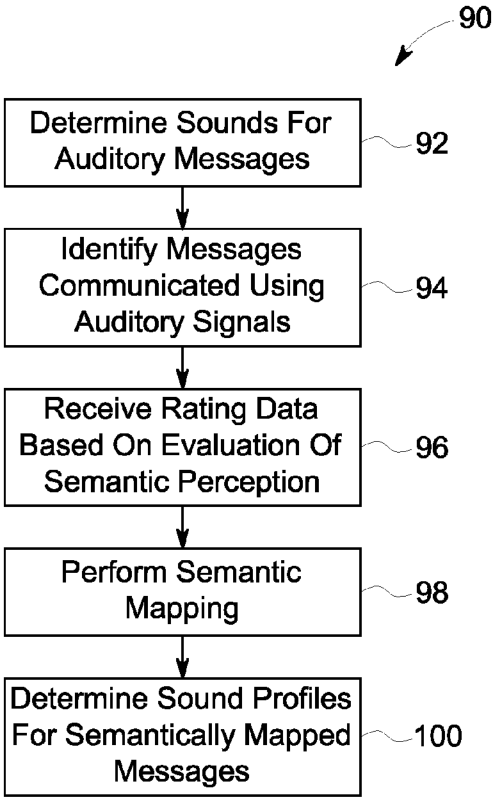
FIG. 5 is a flowchart of a method for generating auditory messages or notifications in accordance with various embodiments.

Various embodiments provide a method 90 as shown in FIG. 5 for generating auditory messages or notifications, such as audible alarms or warning for medical imaging systems or devices. In particular, the method 90 may define auditory signals used in medical devices that specify physical properties such as spectral frequency, duration and temporal sequence, and which convey varying degrees of urgency, as well as the particular medical conditions.

The method 90 generally provides a semantic mapping of different message types to define sound profiles for use in generating audible alarms or warnings. Specifically, the method 90 includes determining a plurality of sounds for auditory messages at 92. For example, different sounds may be provided based on defined standards, known alarm or warning sounds or arbitrary sounds or sounds combinations. In one embodiment, thirty sounds are determined including (i) an IEC low-urgency alarm, (ii) an IEC high-urgency alarm, variations of IEC standards for low, medium and high urgency alarms obtained by manipulating musical properties such as timbre, attack, sustain, decay and release and (iii) arbitrary sounds, such as new sound creations of a sound designer.

The method 90 also includes identifying messages communicated using auditory signals at 94. For example, different messages may be identified based on the particular application or environment. In one embodiment, the messages are medical messages, such as thirty medical messages typically communicated using auditory signals determined based on messages used for ventilators, monitors and infusion pumps, among other devices. The medical message may include, for example, patient and device issues spanning a range of severity/urgency.

Thereafter, rating data is received at 96 based on an evaluation of semantic perception. For example, sounds may be presented to a group, such as a group of nurses, using any suitable auditory means (e.g., computer with headphones) for rating. Additionally, semantic differential rating scales may be provided, for example, which in one embodiment, includes eighteen word pairs that span or encompass a range of semantic content including the key alarm attribute of urgency. The rating data may be collected and or received using, for example, an online data collection tool accessed via a laptop computer. Accordingly, medical messages may be displayed within a rating tool and sounds presented independently.

The data may be received from small groups, such as of four or five subjects. Different methods may be used, such as presenting the sounds and medical messages in separate blocks, half of the groups hearing sounds first. In some embodiments, sounds and medical messages are presented in quasi-counterbalanced orders across groups, for example, in four quasi-counterbalanced orders. It should be noted that in various embodiments, each sound and each message appears equally often in the first, second, third and fourth quarter of the sequence. In some embodiments, the order of stimuli in each quarter of the sequence may be reversed for two of the four sequences. Additionally, in various embodiments, all participants are allowed to complete ratings of a given sound before presenting the next sound in the sequence. It should be noted that the rating data may be acquired in different ways and may be based on previously acquired data.

Thereafter, the received rating data is processed or analyzed, which in various embodiments includes performing semantic mapping at 98. In one embodiment, the rating data is processed using (i) a hierarchical cluster analysis of sound and message ratings using an unweighted pair-group average linkage and (ii) a principal components factor analysis of sound and message ratings. It should be noted that the various steps and methods described herein for various embodiments may be performed using any suitable processor or computing machine.

Figure 6:
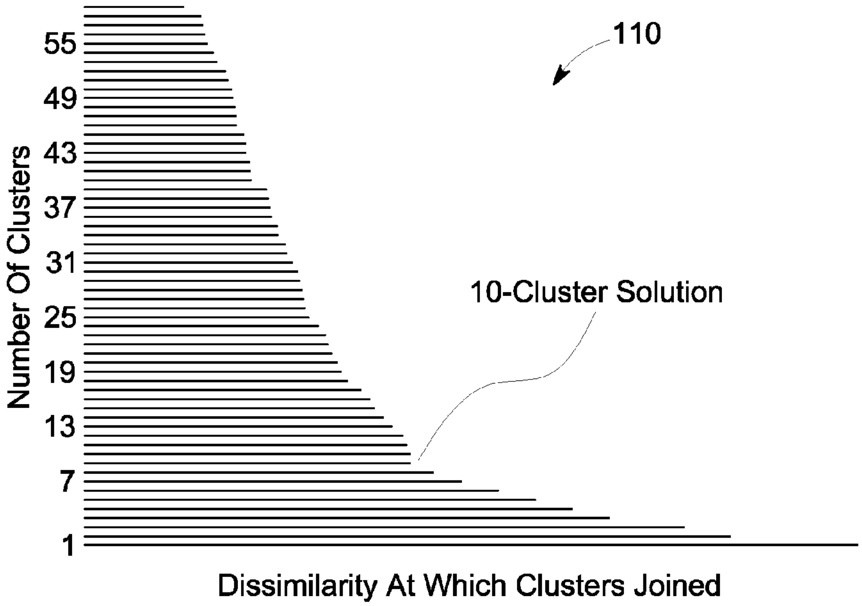
FIG. 6 is a graph illustrating a cluster analysis performed in accordance with various embodiments.

FIG. 6 illustrates a hierarchical cluster analysis using a levels bar chart 110 wherein the vertical axis represents numbers of clusters and the horizontal axis represents the dissimilarity at which clusters joined. The chart 110 shows the levels of dissimilarity at which clusters were joined at each step of the clustering process. As can been seen, the dissimilarity grows larger at a ten cluster solution. Accordingly, in one embodiment, a ten cluster solution is used such that ten message/quality attributes are defined, which as described herein may include seven medical messages and three unassigned messages. The unassigned messages may be used to define additional conditions that are not part of the messages identified at 94. It should be noted that although in one embodiment ten clusters are used to group messages and sounds, different numbers of clusters may be used as desired or needed.

Figure 7:
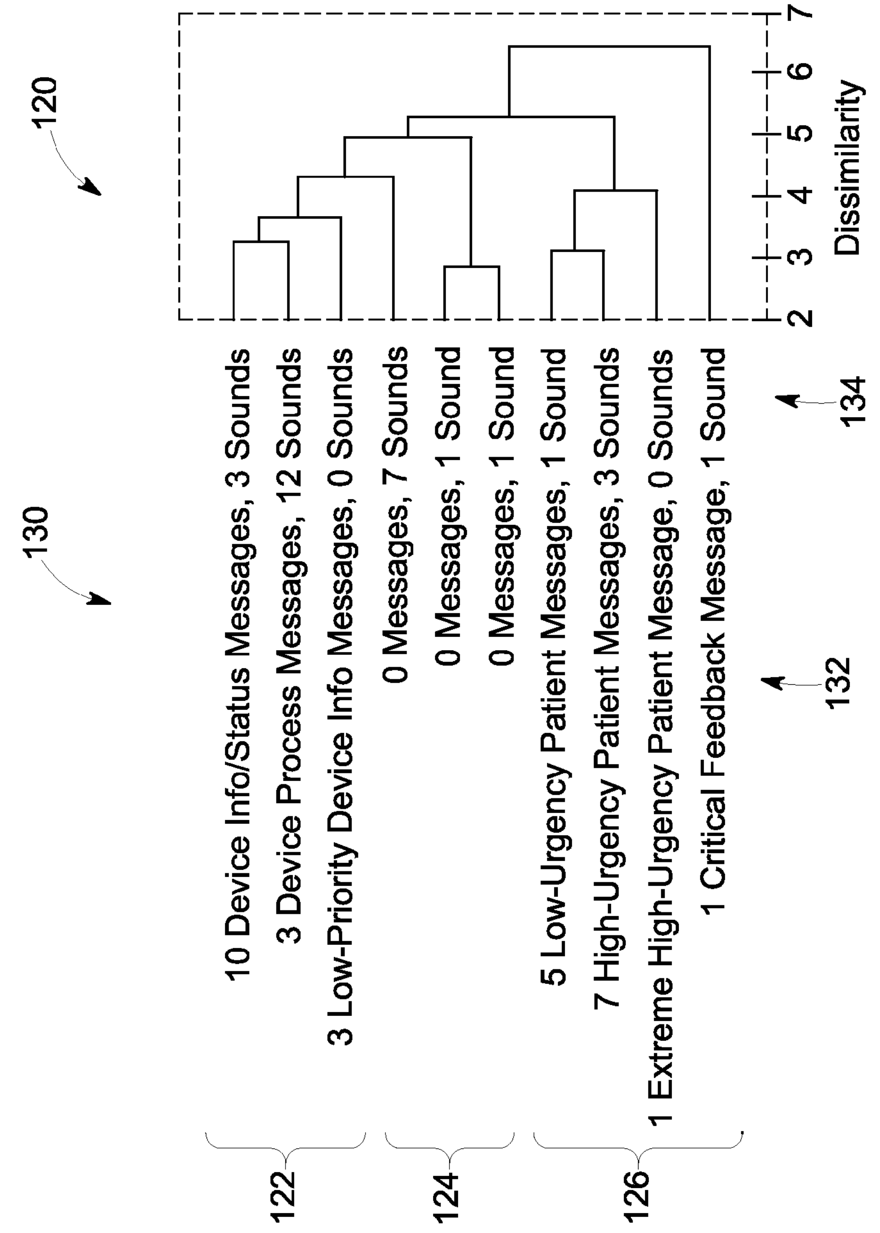
FIG. 7 is a dendrogram in accordance with various embodiments.

FIG. 7 shows a dendrogram 120 illustrating the linkages among the ten clusters 130, which also shows the counts or tallies of messages 132 and sounds 134 within each cluster 130. As can be seen the clusters 130 are divided into groups. In particular, the clusters 130 in the illustrated dendrogram 120 are divided into three major groups: group 122, which are device conditions; group 124, which are sounds that are not associated with any messages; and group 126, which are patient conditions. It should be noted that two clusters 130 of medical messages contain no associated sounds (namely low-priority device info and extremely high-urgency patient message), which may be used to provide new device auditory signals.

Figure 9:
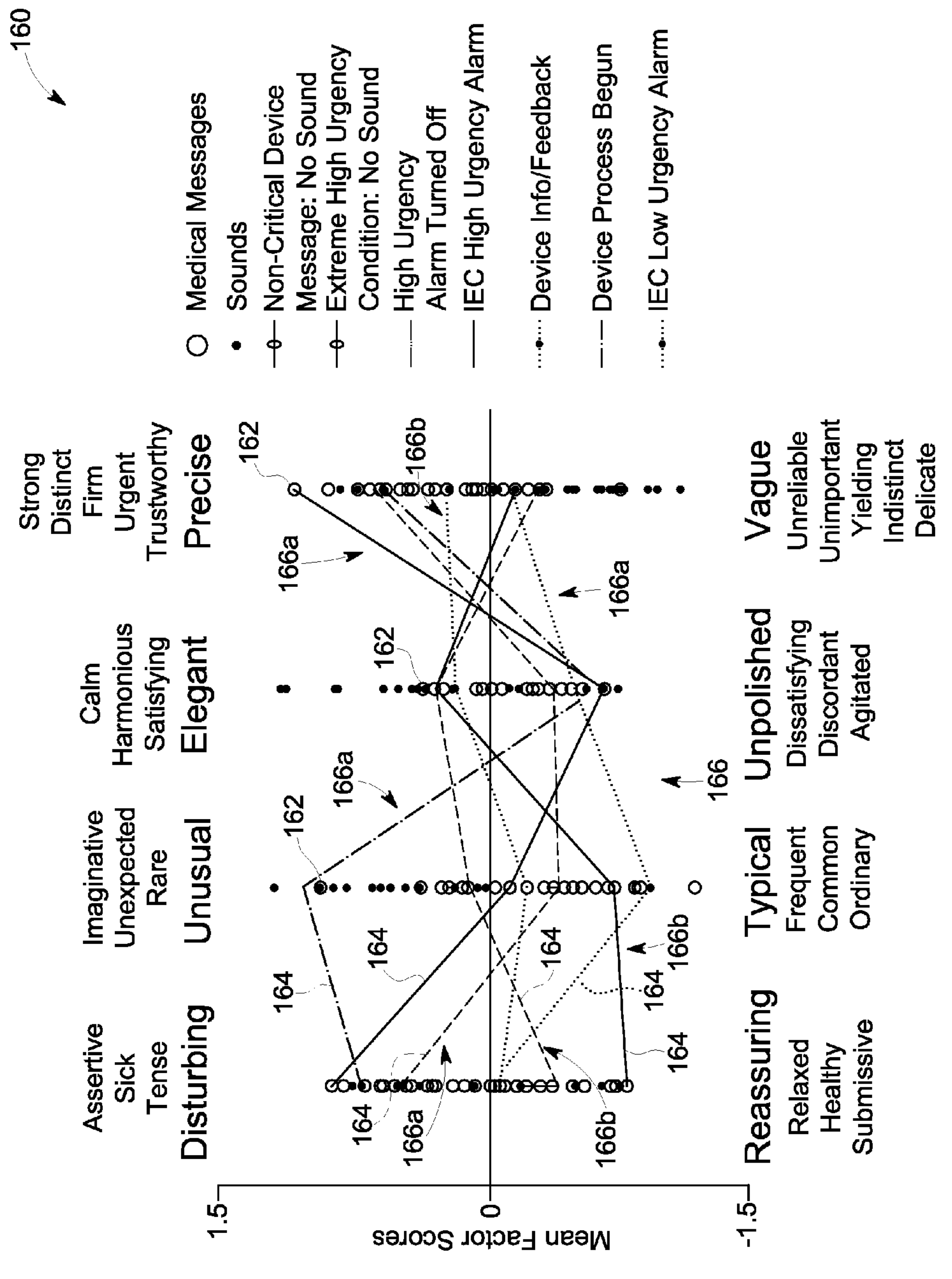
FIG. 9 is a graph illustrating sound profiles determined in accordance with various embodiments.

Additionally, a principal components factor analysis is also performed on the combined rating data for sounds and messages received at 96. The principal components factor analysis in one embodiment uses the Varimax Rotation. It should be noted that Eigen values for the four-factor solution in one analysis exceeded the critical value of 1.00, resulting in a 65.46% of the variance in ratings. The table 140 shown in FIG. 9 illustrates bipolar attribute pairs sorted by factor loadings for each factor. In particular, the column 142 includes the eighteen word pairs that span or encompass a range of semantic content. The columns 144, 146, 148 and 150 are factors (F) that correspond to a set of sound quality differentiating scales that describe the medical auditory design space, which in this embodiment are defined as follows:

F1: Disturbing . . . Reassuring

F2: Unusual . . . Typical

F3: Elegant . . . Unpolished; and

F4: Precise . . . Vague

It should be noted that the table 140 shows attribute pairs sorted according to highest load factors. In particular, attributes loading highest on Factor 1 reflect variation in the Disturbing (Tense, Sick, Assertive) quality of sounds and messages. Accordingly, in some embodiment, sounds nearest the Disturbing end of Factor 1 are most discordant whereas sounds nearest the Reassuring end of Factor 1 are most harmonious. Attributes loading highest on Factor 2 reflect variation in the Unusual (Rare, Unexpected, Imaginative) quality of sounds and messages. Sounds nearest the Typical end of Factor 2 are traditional alarms whereas sounds nearest the Unusual end of Factor 2 are most unlike typical alarms. It should be noted that many messages tend to be Typical. Attributes loading highest on Factor 3 reflect variation in the Elegant (Harmonious, Satisfying, Calm) quality of sounds and messages. Accordingly, in some embodiments, sounds nearest the Elegant end of Factor 3 are most resolved (i.e., sound musically complete) whereas sounds nearest the Unpolished end of Factor 3 are most unresolved (i.e., musically incomplete). Attributes loading highest on Factor 4 reflect variation in the Precise (Trustworthy, Urgent, Firm Distinct, Strong) quality of sounds and messages. Accordingly, in some embodiments, sounds nearest the Precise end of Factor 4 have the hardest "attack", a musical quality describing the force with which a note is struck, whereas sounds nearest the Vague end of Factor 4 have the softest attack. It should be noted that the attribute of Urgency traditionally associated with alarm quality loads on Factor 4. Additionally, it should be noted that Perceived Urgency is shown to relate to the force with which a sound is presented and is independent of the Disturbing quality reflected in Factor 1 in the illustrated embodiment.

Referring again to FIG. 5, the method 90 also includes determining sound profiles at 100 for the semantically mapped messages, namely resulting from the semantic mapping performed at 98. Thus, in various embodiments, semantic profiles of objects representing each of the clusters of messages may be determined. In particular, in one embodiment, factor scores are averaged (across subjects) for each sound and each medical message, which is illustrated in the graph 160 shown in FIG. 9. In the graph 160, the vertical axis represents mean factor scores and the horizontal axis corresponds to each of the different factors that are discrete points along the horizontal axis. Thus, the graph 160 shows each sound and medical message plotted as a function of each factor. It should be noted that the medical messages are indicated by the outline circles 162. For each of the medical messages a line or curve 164 connects the points of seven objects, one from each cluster of messages, which define profiles 166 visualizing the semantic character for each cluster.

The profiles 166*a* represent the four clusters associated with "Patient Conditions". As can be seen, with one exception, these profiles 166*a* are characteristically Disturbing, Typical, Unpolished and Precise. The exception is the "Extreme High Urgency Message", which is defined as highly Unusual. Also, as the criticality of messages increases, the profiles 166 shift toward more Disturbing, Unusual and Precise. The profiles 166*a* for Low-urgency and High-urgency patient messages correspond to IEC standards. However, there is no IEC sound for "Extreme high-urgency message" indicating that a more Disturbing (discordant) and Precise (hard attack) sound may be used to accommodate this level of criticality. The sound for "critical alarm turned off" also does not correspond to an IEC standard and is highly Unusual in sound. It should be noted that the capitalized terms correspond to the scale descriptors. In various embodiments, sound properties included with or within one or more standards, for example IEC standards, may be instantiated in other sounds that are not standards.

The profiles 166*b* represent the three clusters associated with "Device Info/Status". As can be seen, compared to Patient Conditions, these profiles 166*b* tend to be more Reassuring, Elegant and Vague. It should be noted that the profile 166*b* for "Non-critical device info" is another message for which there are no associated sounds. A sound fitting this profile may be highly Reassuring (harmonious), as Typical as the Low-urgency alarm sound, more Elegant (resolved) than current alarms and more Vague (softer attack) than all but the low-urgency alarm. The profile 166*b* for the cluster Device Info/Status tends to be more Precise (harder attack) than the other two profiles 166*b*.

Thus, the graph 160 illustrates a conceptual framework for defining medical messages wherein the quality of sounds map to each of the categories of medical messages, which in the illustrated embodiment is seven messages. The graph 160 shows that various embodiments use conceptual categories (illustrated as terms 168) wherein description qualities describe sounds and different musical qualities can be associated with these terms. It should be noted that different sounds qualities may be used as desired or needed or as defined. Accordingly, the sound profiles 166 provide for the sounds to be described in four-dimensions, namely four independent and inherently meaningful semantic dimensions. Using the sound profiles 166, sounds may be created for different audible notifications, such as audible alarms or warnings.

FIG. 10 is a table 168 illustrating a tabular approximation of the mapping corresponding to the graph 160 shown in FIG. 9. The column 169 corresponds to the medical message of quality attributes associated with the profiles 166 (shown in FIG. 9) and the columns 171, 173, 175 and 179 correspond to the factors (F) defining the sets of sound quality differentiating scales that describe the medical auditory design space (and correspond to the factors of columns 144, 146, 148 and 150 shown in FIG. 8). The cells within each of the factor columns 171, 173, 175 and 179 generally indicate the mean factor score for each factor corresponding to each of the medical messages. In particular, "low" generally corresponds to a score in the bottom third of the mean factor scores, "medium" generally corresponds to a score in the middle third of the mean factor scores and "high" generally corresponds to a score in the top third of the mean factor scores.

In operation or implementation, the audible indications/messages may be selected and implemented based on a medical device by medical device basis. Thus, in one embodiment, a suite of medical devices all installed in the same room will produce a distinct set of sounds that enable the clinician to immediately identify the medical device, the urgency of the alarm, and/or the medical reason the alarm is being generated.

In the various embodiments, a set of candidate audible indications/messages, spanning a range of acoustical/musical properties that may be used for messaging is implemented for each selected medical device 16. Each sound produced by each medical device 16 may have a different acoustic property that identifies the medical device 16 generating the sound. As discussed above, the acoustic properties may include, for example, timbre, frequency, tonal sequence, or various other sound properties. The sound properties are may be selected based on the audible perception of the clinicians who will hear the sounds. For example, an urgent alarm condition may be indicated by generating a sound that has a relatively high frequency. Whereas, a sound used to indicate a status condition may have a relatively low frequency, etc.

Thus, each audible indication 34 generated by a medical device 16 may be described using a vocabulary of attribute words that describe the semantic qualities of audible indications. Accordingly, each audible indication 34 may be selected that has a specific meaning to the clinician, for example, what is the medical device generating the audible indication 34 and what is the medical condition indicated by the audible indication 34. Each audible indication/message or sound therefore may be tailored to human perception such that the sound communicates to the clinician what problem has occurred. For example, a high frequency sound may have a first effect on the listener, and a low frequency may have a different effect on the listener. Therefore, as discussed above, a high frequency sound may indicate that urgent or immediate action is required. Whereas, a low frequency sound may indicate that a patient needs to be monitored.

Because each sound has multiple properties, humans may listen to multiple properties simultaneously. Therefore, each sound can communicate at least two pieces of information to the clinician. For example, a first audible indication may have a first frequency and a first tone indicating that an urgent action is indicated at the heart monitor. Moreover, a second different audible indication may have the first frequency and a second tone indicating that an urgent action is indicated by the respiratory monitor, etc. Thus, a portion of some of the audible indications may be similar to each other, but also include different characteristics to identify the specific medical device, urgency, condition, etc.

As described in more detail herein, the audible indications 34 may be defined and/or tested prior to implementation using a sample of potential users to quantify the semantic qualities of each medical message as described herein. The semantic qualities of each sound may be measured using measurement scales based upon attribute words. The attribute words may include, for example, tone, timbre, frequency, etc. The attribute words describing each sound may then be correlated with one another to produce clusters of words that represent common underlying semantic concepts, for example, urgency, etc. Each medical message, or audible indication 34, is measured with respect to each semantic concept producing a multi-dimensional profile for each message. Potential users may then be used to quantify the semantic qualities of each sound using measurement scales based upon attribute words. The attribute words may then be clustered with one another to reduce a quantity of words and to reduce the quantity of clusters that represent common underlying semantic concepts. Acoustical/musical properties correlated with each concept may then be identified. Moreover, medical messages and sounds that share common semantic profiles may then be identified. Additionally, musical/acoustical properties that characterize each semantic concept and used to create new sounds that communicate similar medical messages may be identified.

Figure 11:
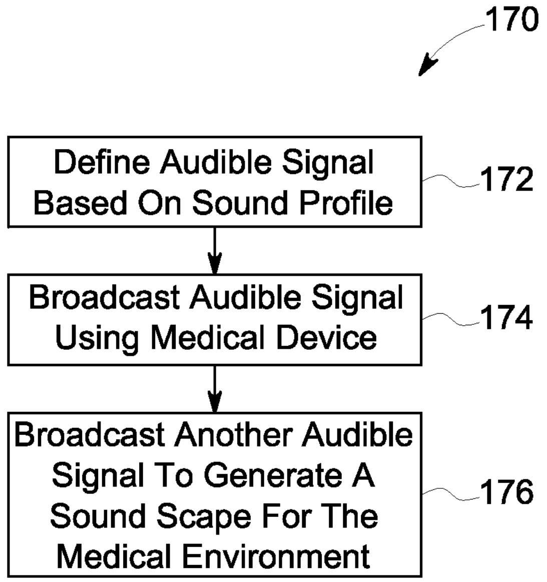
FIG. 11 is a flowchart of a method for generating audible medical messages in accordance with various embodiments.

The sounds defined by the profiles 166 may be used to generate audible messages. For example, a flowchart of a method 170 for generating audible messages in accordance with various embodiments is shown in FIG. 11. In the exemplary embodiment, the method 170 includes defining an audible signal based on the sound profile at 172. For example, a complex audible signal may be generated to include an acoustical property that denotes a medical device and a different second acoustical property that denotes an action to be taken by an operator based on the complex audible signal. The second acoustical property may have has a frequency, timbre or pitch that indicates an urgency of the audible signal. However, the audible signal may have only a single acoustical property or additional acoustical properties. The method 170 also includes broadcasting the audible signal using the medical device at 174.

The method 170 may further include broadcasting at 176 another signal using a different second medical device to generate a soundscape for a medical environment. In operation, the audible signal enables an operator to identify a medical message, as well as the medical device that broadcast (e.g., emitted) the audible signal. The audible signal may also indicate a movement of a medical device in some embodiments. The audible signal is configured to audibly convey semantic characteristics indicative of the medical device.

Figure 12:
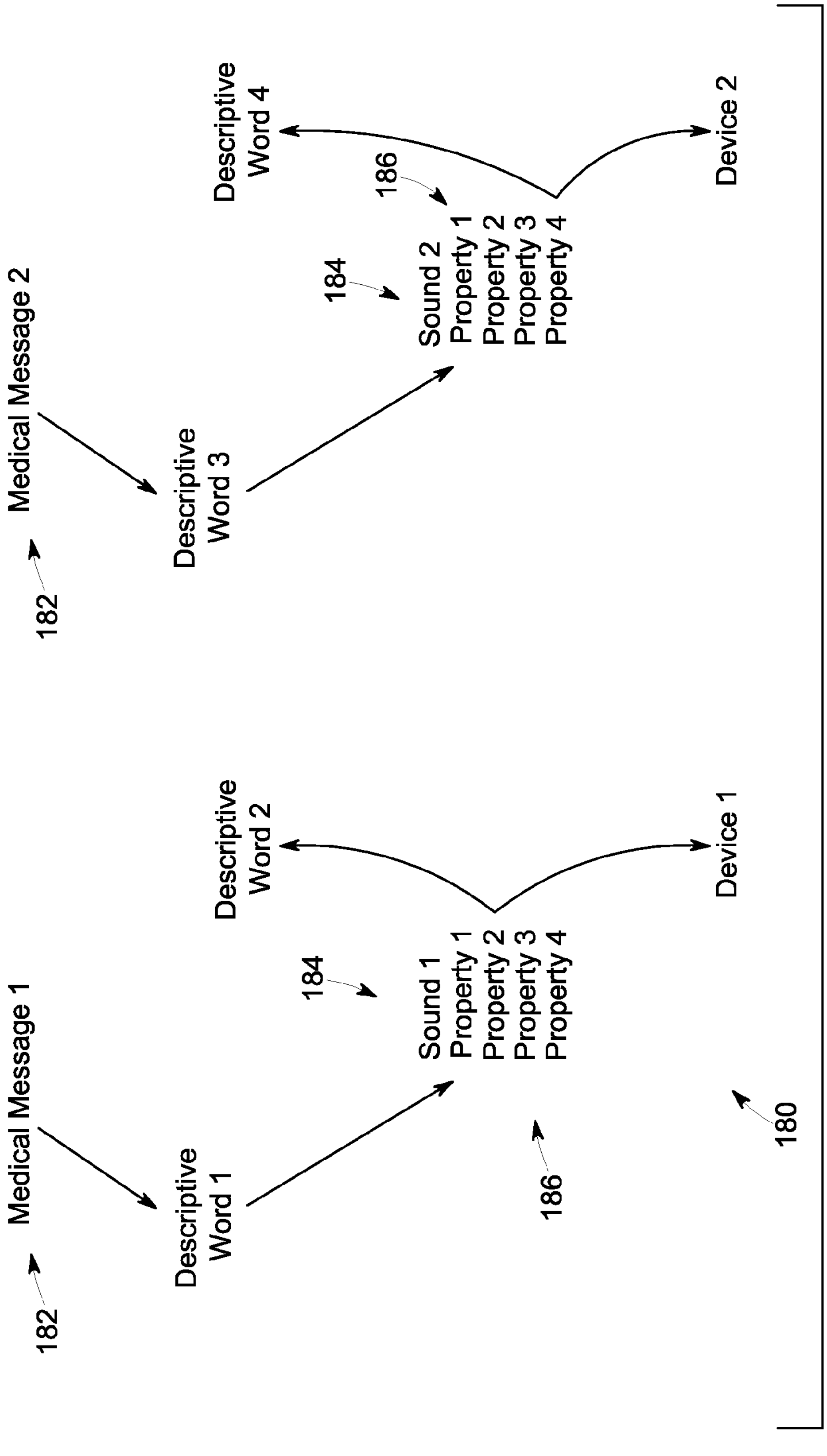
FIG. 12 is a diagram illustrating a method of aligning or correlating a medical message to a sound in accordance with various embodiments.

FIG. 12 is a diagram illustrating a method 180 of aligning or correlating a medical message to a sound. A medical message 182 is the information that is intended to be communicated to the operator, which is separate from the sound 184 that is used to communicate the message 182. The message 182 is correlated with the sound 184 using descriptive words that lie therebetween. The descriptive words may be any type of word that correlates the message 182 to the sound 184. In various embodiments, one or more semantic profiles and the correlated sound parameters define categories of messages (e.g., urgent patient condition).

In the exemplary embodiment, each sound 184 has multiple properties 186 that may be aligned or correlated with different words in the vocabulary. The descriptive words or attributes may be, for example, loud, large, sharp, good, pleasant, etc. The attributes may also be used to describe the messages. Accordingly, various embodiments disclosed herein provide a means to define a common set of attributes that describe the message 182 and the sounds 184 and then use these attributes to relate the message 182 to the sounds 184 in a language that is understood by the user.

Examples of messages may also include, for example, blood pressure is high, CO2 is high, blood pressure is low, etc. The sound properties 186 include, for example, the auditory frequency of the sound, the timbre, is the sound pleasing to the operator, is the sound elegant, musical properties, such as is the note flat, is the tone melodic, etc. These sound properties 186 enable the user to distinguish between different sounds 184. Thus, the sounds 184 generated relate a message 182 and have an intrinsic meaning to the users of the medical equipment. Thus, various embodiments align the intrinsic meaning of the sound 184 with the message 182. For example, the sound may have an intrinsic meaning that there is a problem in the vasculature.

It should be realized that a single medical message 182 may be correlated with one or more sounds 184 using one or more descriptive words because humans can distinguish multiple sound qualities concurrently. For example, medical message 1 has a descriptive word that is particularly descriptive of message 1 and is correlated with a property 1 of sound 1. There may be other descriptive words used to describe message 1, but not associated with the medical connotation, and still used to describe other aspects, such as the device emitting the sound.

Thus, various embodiments may be used to generate unique sounds that denote medical messages/conditions and devices. Individual medical messages/conditions and individual devices are mapped to specific sounds via common semantic/verbal descriptors. The mapping leverages the complex nature of sounds having multiple perceptual impressions, connoted by words, as well as multiple physical properties. Certain properties of sounds are aligned with specific medical messages/conditions whereas other properties of sounds are aligned with different devices, and may be communicated concurrently, simultaneously or sequentially.

Various embodiments may define sounds that relate a particular medical message to a user. Specifically, descriptive words are used to relate or link medical messages to sounds. Various embodiments also may provide a set or list of sounds that relate the medical message to a sound. Additionally, various embodiments enable a medical device user to differentiate alarm/warning sounds on the basis of acoustical/musical properties of the sounds. Thus, the sounds convey specific semantic characteristics, as well as communicate patient and system status and position through auditory means.

At least one technical effect of various embodiments is increased effectiveness or efficiency with which a user responds to audible indications.

It should be noted that the various embodiments, for example, the modules described herein, may be implemented in hardware, software or a combination thereof. The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive, optical disk drive, solid state disk drive (e.g., flash drive of flash RAM) and the like. The storage device may also be other similar means for loading computer programs or other instructions into the computer or processor.

As used herein, the term "computer" or "module" may include any processor-based or microprocessor-based system including systems using microcontrollers, reduced instruction set computers (RISC), application specific integrated circuits (ASICs), logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments. The set of instructions may be in the form of a software program. The software may be in various forms such as system software or application software. Further, the software may be in the form of a collection of separate programs, a program module within a larger program or a portion of a program module or a non-transitory computer readable medium. The software also may include modular programming in the form of object-oriented programming. The processing of input data by the processing machine may be in response to user commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions and types of materials described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the various embodiments, including the best mode, and also to enable any person skilled in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal languages of the claims.

What is claimed is:

1. A method for generating an audible medical message, the method comprising using at least one processor to:

receive defined message categories corresponding to one or more medical alarms or conditions of plural different medical devices from the medical devices;

receive semantic rating scale data corresponding to different sounds, the semantic rating scale data representative of one or more previous evaluations of perception of the different sounds;

perform semantic mapping using the defined message categories and the semantic rating scale data that are received, the semantic mapping associating the defined message categories with the different sounds;

determine sound profiles of audible medical messages based on the semantic mapping, wherein the sound profiles are determined by combining two or more of the different sounds to form a complex audible signal, wherein each of the audible medical messages includes different acoustical properties that differ for each of an alarm condition, a warning condition, a status condition, and movement for each of the medical devices; and direct the different medical devices to audibly generate the two or more of the different sounds of the complex audible signal based on the sound profiles that are determined.

2. The method of claim 1, wherein the at least one processor including the at least one memory is further used to perform a hierarchical cluster analysis of the semantic rating scale data that is received to identify a set of clusters of the different sounds and medical message descriptions based on semantic profiles for use in performing the semantic mapping.

3. The method of claim 2, wherein the hierarchical cluster analysis comprises an unweighted pair-group average linkage.

4. The method of claim 3, wherein the at least one processor including the at least one memory is further used to generate a dendrogram of one or more of the linkages among the sets of clusters.

5. The method of claim 1, wherein the at least one processor including the at least one memory is further used to perform a principal component analysis of the semantic rating scale data that is received.

6. The method of claim 1, wherein the semantic rating scale for the different sounds comprises sound quality differentiating scales and further comprising averaging factor scores for each of the different sounds and medical message descriptions.

7. The method of claim 6, wherein the sound quality differentiating scales represent different auditory characteristics.

8. The method of claim 1, wherein the semantic mapping comprises mapping each of several different medical message descriptions to the different sounds.

9. A method for generating an audible medical message, said method comprising using at least one processor to:

determine one or more alarms or conditions of plural different medical devices concurrently performing different functions;

define different first and second sets of audible signals for the different medical devices based on the different one or more alarms or conditions, wherein the first and second sets of audible signals are defined by combining one or more sounds with one or more medical messages for each of the first and second sets of audible signals, wherein the first set of audible signals for a first medical device of the different medical devices differs from the second set of audible signals for a second medical device of the different medical devices, wherein each of the audible signals in the first and second sets includes an acoustical property based on a semantic sound profile that corresponds to the medical message for a corresponding medical device of the first and second medical devices, wherein the acoustical property has at least one of a frequency, timbre, attack or pitch that indicates an urgency of the audible signal, and wherein the acoustical property is different for each different level of urgency and for each corresponding medical device of the first and second medical devices; and directing the first medical device to audibly broadcast the first set of audible signals and the second medical device to audibly broadcast the second set of audible signals, wherein at least one of the first or second sets of audible signals indicates movement of the corresponding first or second medical device.

10. The method of claim 9, wherein at least one of the first or second sets of audible signals represents semantic characteristics indicative of at least one of the different medical devices broadcasting the at least one of audible signals or the medical messages.

11. A medical arrangement comprising:

one or more first processors; and a plurality of medical devices configured to generate different medical messages, each of the medical devices including one or more second processors and one or more speakers, wherein the one or more first processors are configured to monitor operations of the medical devices, determine audible signals by combining sounds for each of the audible signals, and communicate with the medical devices to direct the medical devices to audibly generate the audible signals, wherein the one or more second processors in each of the medical devices is configured to audibly generate the audible signal of the corresponding medical device, the audible signal representative of the medical messages and having one or more of a frequency, timbre or pitch representative of an urgency of the medical messages, wherein the audible signal is different for different levels of urgency of the medical devices and for each of the medical devices, and wherein the audible signal individually identifies the medical devices and the medical messages based only on the audible signals, wherein the audible signals indicate movement of the medical devices.

12. The medical arrangement of claim 11, wherein the audible signals are configured to audibly convey semantic characteristics indicative of at least one of statuses of the medical devices or a status of a patient.

13. The medical arrangement of claim 11, wherein the medical devices are located within a single room of a healthcare facility.

14. A method for generating an audible medical message, said method comprising using at least one processor including at least one memory to:

receive inputs from different medical devices;

determining different sets of complex audible signals for the different medical devices by combining different sounds for each of the sets of the complex audible signals, wherein a first set of the sets of complex audible signals for a first medical device differs from a second set of the sets of audible signals for a second medical device, wherein each of the complex audible signals includes an acoustical property that denotes a different medical device of the medical devices that audibly generates the complex audible signal and a different second acoustical property that denotes a message to be responded to by an operator based on the complex audible signal, wherein the second acoustical property has one or more of a frequency, timbre, attack or pitch that indicates an urgency of the audible signal, wherein the acoustical property is different for each different level of urgency; and broadcast the complex audible signals using the different medical devices, wherein at least one of the complex audible signals indicates movement of the medical devices.

15. The method of claim 14, wherein the at least one processor including the at least one memory is further used to broadcast at least one of the complex audible signals using a different second medical device to generate a soundscape for a medical environment.

16. The method of claim 14, wherein at least one of the complex audible signals individually identifies a particular medical device based only on a particular one of the at least one of the complex audible signals.

17. The method of claim 14, wherein at least one of the complex signals is configured to audibly convey semantic characteristics indicative of both the medical device and the medical message.

18. A system comprising:

one or more processors configured to monitor plural different medical devices performing different medical functions on a patient, the one or more processors configured to determine different acoustic sounds for each of the different medical devices to audibly generate based on outputs of the different medical devices, wherein the one or more processors are configured to communicate with the different medical devices to direct the different medical devices to audibly generate the different acoustic sounds to identify the different medical devices, wherein the one or more processors are configured to monitor movements of the different medical devices and direct the different medical devices to audibly generate the different acoustic sounds to represent the movements of the different medical devices.

19. The system of claim 18, wherein the system includes the different medical devices and the different medical devices include an imaging device and one or more of a medical delivery device or a medical monitoring device.

* * * * *